United States Patent
Veksler

(10) Patent No.: US 11,238,304 B2
(45) Date of Patent: Feb. 1, 2022

(54) SYSTEM AND METHOD FOR BIOMETRIC IDENTIFICATION

(71) Applicant: QUANTUM RGB LTD., Rosh HaAyin (IL)

(72) Inventor: Henia Veksler, Michmanim (IL)

(73) Assignee: QUANTUM RGB LTD., Rosh HaAyin (IL)

( * ) Notice: Subject to any disclaimer, the term of this patent is extended or adjusted under 35 U.S.C. 154(b) by 0 days.

(21) Appl. No.: 16/492,422

(22) PCT Filed: Feb. 25, 2018

(86) PCT No.: PCT/IL2018/050213
§ 371 (c)(1),
(2) Date: Sep. 9, 2019

(87) PCT Pub. No.: WO2018/163153
PCT Pub. Date: Sep. 13, 2018

(65) Prior Publication Data
US 2020/0057908 A1    Feb. 20, 2020

Related U.S. Application Data

(60) Provisional application No. 62/468,398, filed on Mar. 8, 2017.

(51) Int. Cl.
G06K 9/52    (2006.01)
G06T 7/246    (2017.01)
G06K 9/00    (2006.01)

(52) U.S. Cl.
CPC ......... *G06K 9/522* (2013.01); *G06K 9/00926* (2013.01); *G06T 7/246* (2017.01);
(Continued)

(58) Field of Classification Search
CPC ............... G06K 9/522; G06K 9/00926; G06K 9/00771; G06K 9/6201; G06T 7/246;
(Continued)

(56) References Cited

U.S. PATENT DOCUMENTS 9,443,320 B1* 9/2016 Gaidon ................ G06K 9/3233
2003/0059124 A1* 3/2003 Center, Jr. ......... G06K 9/00275
382/278
(Continued)

OTHER PUBLICATIONS

Face Spoofing Detection Based on Color Distortion (Year: 2017).*
(Continued)

*Primary Examiner* — Nizar N Sivji
(74) *Attorney, Agent, or Firm* — Pearl Cohen Zedek Latzer Baratz LLP

(57) ABSTRACT

The present invention relates to a method for generating a biometric signature of a subject comprising: obtaining a plurality of sequential video frame images of a moving subject from a video segment; obtaining a portion of each frame comprising a surrounding of the moving subject; carrying out a transformation function to the frequency domain on one or more of said portions of the frames comprising a surrounding of a of the subject; and optionally saving the spectral characteristics of said transformation function in a repository. The present invention also relates to a system for carrying out said method.

19 Claims, 12 Drawing Sheets

(52) U.S. Cl.
CPC ............... *G06T 2207/10016* (2013.01); *G06T 2207/30196* (2013.01)

(58) Field of Classification Search
CPC ........... G06T 2207/10016; G06T 2207/30196; G16H 40/63; G16H 10/60; H04N 7/18
See application file for complete search history.

(56) References Cited

U.S. PATENT DOCUMENTS

| | | | | |
|---|---|---|---|---|
| 2009/0315996 | A1* | 12/2009 | Guler | G06K 9/00671 348/169 |
| 2010/0128939 | A1* | 5/2010 | Stubler | G06K 9/00281 382/118 |
| 2011/0170785 | A1* | 7/2011 | Ushijima | G06T 7/74 382/195 |
| 2011/0194762 | A1* | 8/2011 | Haibing | G06K 9/00281 382/165 |
| 2012/0072121 | A1* | 3/2012 | Mollicone | G16H 40/67 702/19 |
| 2013/0201329 | A1* | 8/2013 | Thornton | H04N 7/18 348/143 |
| 2014/0247362 | A1* | 9/2014 | Li | G06T 7/254 348/159 |
| 2015/0138332 | A1* | 5/2015 | Cheng | H04N 7/18 348/77 |
| 2015/0304634 | A1* | 10/2015 | Karvounis | H04N 5/2224 348/46 |
| 2016/0140407 | A1* | 5/2016 | Veksler | G06K 9/6215 348/77 |
| 2016/0321671 | A1* | 11/2016 | Chandrasekaran | G06K 9/00255 |
| 2017/0323167 | A1* | 11/2017 | Mapen | G06T 7/90 |

OTHER PUBLICATIONS

Murase, H. et al., Moving object recognition in eigenspace representation: gait analysis and lip reading, Pattern Recognition Letters, Elsevier, Amsterdam, NL, vol. 17, No. 2, Feb. 8, 1996, pp. 155-162.
European Search Report for EP Appl. No. 18764240.0 dated Oct. 22, 2020.

* cited by examiner

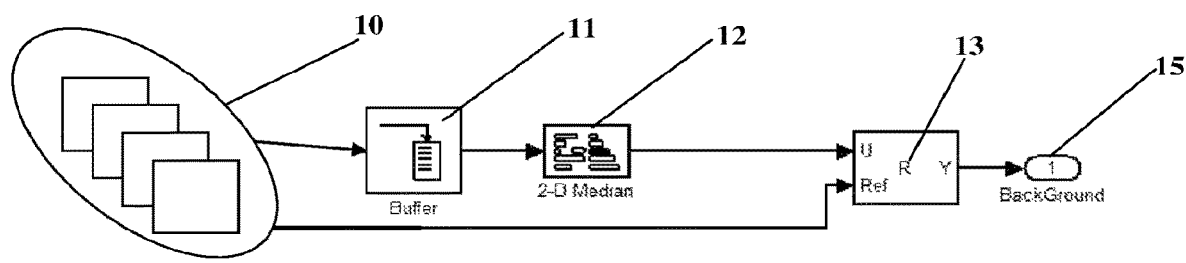
FIG 3A
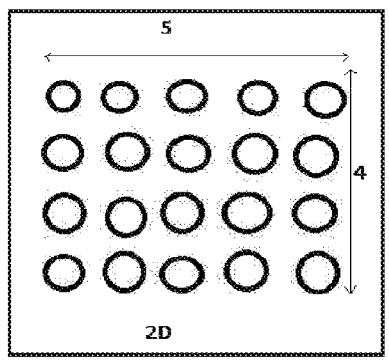
FIG 3B
FIG 3C
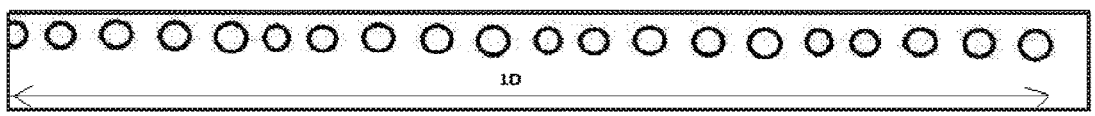

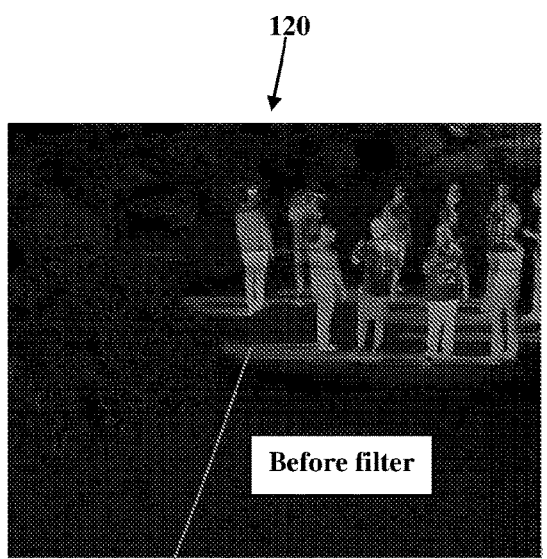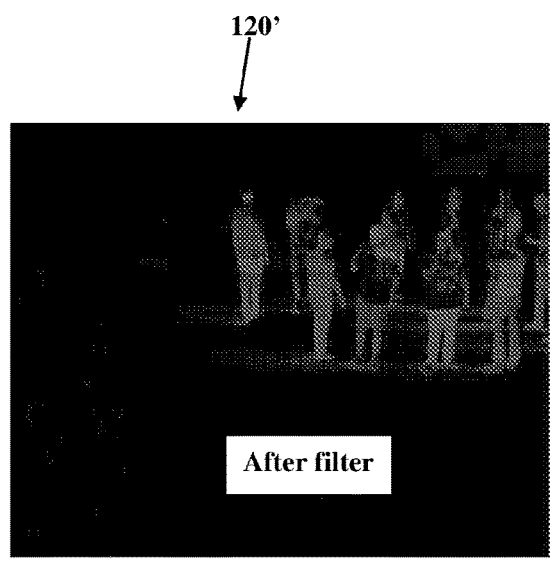
FIG 4C
FIG 4D

SYSTEM AND METHOD FOR BIOMETRIC IDENTIFICATION

CROSS-REFERENCE TO RELATED APPLICATIONS

This application is a National Phase Application of PCT International Application No. PCT/IL2018/050213, International Filing Date Feb. 2, 2018, claiming the benefit of U.S. Provisional Patent Application No. 62/468,398, filed Mar. 8, 2017, which are hereby incorporated by reference in their entireties.

FIELD OF THE INVENTION

The present invention relates to the field of biometric identification through image and signal processing. More particularly, the present invention relates to the identification of a person by spectrum analyzing of a moving person's surrounding.

BACKGROUND OF THE INVENTION

Current biometric methods for the image identification of a subject are based on clear facial, iris, handprints etc., and require special equipment and clear photographs from specially installed cameras. Several biometric methods are ineffective when used with standard security cameras since they have a relatively low resolution, they are placed at generally high angles and function with uncontrolled lighting conditions. One of the outcomes of these drawbacks is that the people identification from these cameras are inefficient. Today, tracking methods are based on the fact that a camera can track certain objects until the objects exit that camera's field of view. When a person exits a certain camera's field of view and enters an adjacent camera's field of view the tracking of the first camera is ceased and a new tracking begins by the second camera. The tracking of the second camera is implemented independently, regardless of the first camera tracking. Automatic continuous tracking of a certain object from one camera's field of view to another camera's field of view includes complicated tracking applications which are inaccurate and frequently tend to malfunction. Furthermore, a tracking method which enables tracking even when a subject exits all the camera fields of view (or is obscured by another object) and returns later on, is highly needed.

Furthermore, there is a need for tracking the whereabouts of a person when analyzing a post event video and looking for the timeline of events regarding a specific person. A common solution today is to have a security analyst view the video and mark manually the appearance of a certain individual.

FIG. 1 illustrates a prior art series of cameras (50a-50e) aiming at covering the surrounding field of view of a warehouse. Each camera covers a certain field of view. Each camera's adjacent camera covers a field of view adjacent to its camera's field of view. Security personnel viewing the camera filming recording at a remote location would have difficulties tracking a suspicious subject when the suspicious subject crosses one camera's field of view to another. Current systems allow marking a subject on the camera viewing screen. Then the subject is tracked using appropriate applications until the subject exits the camera's field of view. The security personnel would have to mark the suspicious subject again on the screen of the adjacent camera for continuation tracking, what could be very confusing due to the fact that people look alike on a security camera. Furthermore, constant tracking along a series of cameras requires frequent manual interference.

Also, means are required for tracking and identifying a subject even if he exits all system cameras field of view for a long period of time.

US20110194762 relates to a method for detecting a hair region, includes acquiring a confidence image of a head region; and detecting the hair region by processing the acquired confidence image. The hair region detection method may detect the hair region by combining skin color, hair color, frequency, and depth information.

WO2014/203248 provides certain solutions to the aforementioned problems. This publication relates to a method and system for generating and comparing a biometric singular signature of a person comprising the steps of a) obtaining a first image of a person; b) obtaining a hair portion image of the person; c) transforming the hair portion image into its frequency domain image and optionally saving said frequency domain image in a database. However, the detection process in this publication necessitates obtaining an image with a clear portion of a person's hair and/or head contour in order to carry out the detection.

It is therefore an object of the present invention to provide a method and means for coherent identification of a person with a novel biometric quality based on his effect on the surroundings.

It is yet another object of the present invention to provide a method and means for generating a digital signature accordingly.

It is yet another object of the present invention to provide a method and means for performing a signature on a subject and means for identifying the signed subject later on when returning to system cameras fields of view.

It is yet another object of the present invention to provide means to analyze a post event video to determine the whereabouts of a specific person during the Video run time.

It is yet another object of the present invention to generate a signature for a person from a first video sequence and search for that specific person in a second video sequence, generated at a different time, on-line or post event analysis.

Other objects and advantages of the present invention will become apparent as the description proceeds.

SUMMARY OF THE INVENTION

The present invention relates to a method and system for obtaining a biometric identification of the frequency spectral characteristics of a surrounding area of a moving subject person. The preset invention comprises obtaining a sequence of video frames and performing image processing to the frames. The frequency spectral characteristics of a surrounding frame portion of the moving person is obtained and may be stored in a database and compared with second frequency spectral characteristics of a surrounding area of a second subject person so as to determine whether an identification therebetween is held positive indicating that the first and second subject persons are actually the same person. The comparison of both frequency spectral characteristics is such that if the coherence level therebetween is above a predefined threshold—the determination is deemed positive.

The present invention comprises generating a vector according to the movement of the subject person and determining an area—Region Of Interest (ROI)—at a distant position in relation to the generated vector. The ROI is integrated at corresponding locations on each of the sequence frames and a transformation function to the frequency domain is applied thereon. The frequency spectral characteristics obtained therefrom are optionally stored in a database.

The present invention relates to a method for generating a biometric signature of a subject comprising:

obtaining a plurality of sequential video frame images of a moving subject from a video segment;

obtaining a portion of each frame comprising a surrounding of the moving subject;

carrying out a transformation function to the frequency domain on one or more of said portions of the frames comprising a surrounding of the subject; and optionally saving the spectral characteristics of said transformation function in a repository.

Preferably, obtaining a portion of each frame comprising a surrounding of the moving subject comprises:

obtaining foreground frames corresponding to the plurality of sequential video frames, each comprising the moving subject;

generating a vector representing the direction of the moving subject;

determining a Region Of Interest (ROI) at a position in relation to said vector; and determining said portion of each frame comprising a surrounding of the moving subject, at a location on each frame corresponding to the location of said determined ROI.

Preferably, obtaining foreground frames corresponding to the plurality of sequential video frames comprises:

obtaining a background frame comprising the background of the plurality of sequential video frame images;

subtracting said background frame from each of the plurality of sequential video frames.

Preferably, generating a vector representing the direction of the moving subject comprises:

obtaining body portions of the foreground objects of the foreground frames;

obtaining reference point frames corresponding to the foreground frames, each comprising a reference point about or at an edge of the corresponding location of said body portions;

combining all the reference points frames into a three-dimensional coordinate system frame comprising all the reference points being at their corresponding location on the three-dimensional coordinate system frame;

determining a vector in the three-dimensional coordinate system frame according to a sequence of a number of reference points from the reference points, that produce the most stable vector.

Preferably, determining a Region Of Interest (ROI) at a position in relation to said vector comprises:

a. obtaining a plurality of background sequential video frames being a sequence of frames comprising the background of the plurality of sequential video frame images;

b. integrating the vector determined in in each background frame;

c. determining an initial ROI on each background frame being at a predetermined corresponding position from said vector;

d. carrying out a transformation function to the frequency domain in time to the ROI portions of said background frames obtaining spectral characteristics and determining the stability frequencies from said spectral characteristics;

e. integrating each of the plurality of sequential video frame images with said initial ROI determined and carrying out a transformation function to the frequency domain in time to the initial ROI portion of said sequential video frames thus obtaining spectral characteristics and storing the sensitivity of said stability frequencies of said spectral characteristics of the initial ROI;

f. shifting the initial ROI to a surrounding area in each of the plurality of sequential video frame images, and carrying out a transformation function to the frequency domain in time to the currently shifted ROI portion of said sequential video frames thus obtaining spectral characteristics and storing the sensitivity of said stability frequencies of said spectral characteristics of the currently shifted ROI;

g. repeating step f according to a predetermined shifting rule;

h. after step f has been repeated for all sequences of the shifting rule determining the ROI of the initial and shifted ROIs with the highest sensitivity stored as the ROI.

Preferably, the body portions are one or more of:
the head portion;
the center body portion;
the feet portion.

Preferably, the method further comprises a step of identification by comparing the obtained spectral characteristics of the transformation function with spectral characteristics saved in a database, wherein an identification result is deemed to be positive when the coherence level between both compared frequency spectral characteristics is above a certain threshold.

Preferably, the method comprises performing a signature for a subject by obtaining and saving the vector generated and the corresponding ROI portion determined, and further obtaining and saving one or more of the following items in a database in relation to said subject:

the spectral characteristics of a transformation function to the frequency domain in time to the ROI portions of the sequential frames;

the spectral characteristics of a transformation function to the frequency domain in time to the ROI portions of the background frames;

the spatial spectral characteristics of a transformation function to the frequency domain at the ROI portion of one of the sequential frames;

the spatial spectral characteristics of a transformation function to the frequency domain at the ROI portion of one of the background frames.

Preferably, the method further comprises a step of identification;

providing a signature of a subject person stored in a data base comprising a vector, an ROI, spectral characteristics of a transformation function to the frequency domain in time of a frame sequence, spectral characteristics of a transformation function to the frequency domain in time of background frames;

wherein the Region Of Interest (ROI) at a position in relation to the vector is determined such that it is in the same position in relation to the vector as the signature ROI in relation to the signature vector;

wherein said method further comprises:

i. obtaining the spectral characteristics of a transformation function to the frequency domain in time to the ROI portions of the background frames;

ii. obtaining a relative difference by inputting the spectral characteristics of a transformation function to the frequency domain in time of the background frames of step (i) and said signature spectral characteristics of a transformation function to the frequency domain in time of background frames, into a transfer function;

iii. obtaining the spectral characteristics of a transformation function to the frequency domain in time to the ROI portions of the sequence frames and shifting the value of said spectral characteristics of a transformation function to the frequency domain in time to the ROI portions of the sequence frames, in a proportional manner as said relative difference;

iv. comparing the shifted values to the signature spectral characteristics of a transformation function to the frequency domain in time of a frame sequence;

wherein an identification result is deemed to be positive when the coherence level between the compared spectral characteristics of step (iv) is above a predefined threshold.

Preferably, the method further comprises an identification, said method further comprising:

obtaining an error value between the spectral characteristics of the transformation function and spectral characteristics saved in a database;

wherein an identification is deemed positive if one of the following conditions are met:

I) the error value is beneath a predefined threshold value;
II) the following consecutive steps are carried out less times than a predetermined threshold number:
   i. transferring the error value to an adaptive filter that adapts the values of one of the spectral characteristics according to the error value;
   ii. obtaining an error value between the adapted spectral characteristics value and the other spectral characteristics;
   iii. determining if the error value of step (ii) is beneath said threshold value;
   iv. returning to step (i) when the determination of the error value of step (iii) is deemed negative.

Preferably, the method further comprises an identification, said method further comprising:

obtaining an error value between the spectral characteristics of the transformation function and spectral characteristics saved in a database;

wherein an identification is deemed positive if one of the following conditions are met:

I) the error value is beneath a predefined threshold value;
II) the following consecutive steps with possible recursion are fully carried out during a time duration less than a predefined threshold time:
   i. transferring the error value to an adaptive filter that adapts the values of one of the spectral characteristics according to the error value;
   ii. obtaining an error value between the adapted spectral characteristics value and the other spectral characteristics;
   iii. determining if the error value of step (ii) is beneath said threshold value;
   iv. returning to step (i) when the determination of the error value of step (iii) is deemed negative.

The present invention relate to a system comprising one or more cameras connected to processing means, wherein the processing means comprise:

A) a database;
   B) a transformation to frequency domain module;
   C) a comparing frequency coherence function module.

The present invention system processing means is configured to carry out all the method steps described herein (e.g. method steps relating to transformation functions, comparison functions, filtering functions, shifting functions, error functions, absolute value functions, luminance functions, convolution functions, contrast adjusting functions, optimization functions, stable frequency reading functions, frequency sensitivity reading functions, transfer functions, coherence comparison functions, etc.).

The present invention relates to a system comprising one or more cameras connected to processing means, wherein the processing means comprise:

A) a database;
   B) a transformation to frequency domain module;
   C) a comparing frequency coherence function module;

wherein the processing means are configured to generate a biometric signature of a subject comprising the steps of:

obtaining a plurality of sequential video frame images of a moving subject from a video segment;

obtaining a portion of each frame comprising a surrounding of the moving subject;

carrying out a transformation function to the frequency domain on one or more of said portions of the frames comprising a surrounding of the subject; and optionally saving the spectral characteristics of said transformation function in a repository.

BRIEF DESCRIPTION OF THE DRAWINGS

The present invention is illustrated by way of example in the accompanying drawings, in which similar references consistently indicate similar elements and in which:

FIGS. 3A-3C illustrate method steps to obtain a background frame according to an embodiment of the present invention.

FIGS. 4C-4D illustrate using an example filter according to an embodiment of the present invention.

DETAILED DESCRIPTION OF THE INVENTION

Several specific details are provided herein, such as examples of devices/components, and methods, to provide a thorough understanding of embodiments of the present invention. A person skilled in the art will understand, however, that the present invention can be implemented without one or more of the specific details or alternatively, well-known details are not described for the sake of clarity (and would be clearly understood by a person skilled in the art).

Some components disclosed herein may be implemented in hardware, software, or a combination thereof (e.g., firmware). Software components may be in the form of computer-readable program code stored in a computer-readable storage medium (e.g. a memory, mass storage device, removable storage device). For example, a computer-readable storage medium may comprise computer-readable program code for performing the function of a particular component. Likewise, computer memory may be configured to include one or more components, which may be executed by a processor. Software components may be implemented in logic circuits, for example. Components may be implemented separately in multiple modules or together in a single module.

The present invention relates to a method and system for biometric identification of a person by processing the interaction between persons and their surroundings. The present invention comprises obtaining a plurality of sequential video frame images of a person typically moving, obtaining portions of the frames comprising the surrounding of the person in motion and performing spectrum analysis in the frequency range of those portions. The processing of the video frames concludes with a signature of the analysis product and saving the same in a repository. The saved signature may be used for future comparison and recognition verification with another analyzed plurality of video frames, even from a different camera and/or different background. If the other analyzed plurality of video frames is similar to the first (with a level of coherence above a certain threshold in the frequency domain) then a positive identification is determined.

Figure 1:
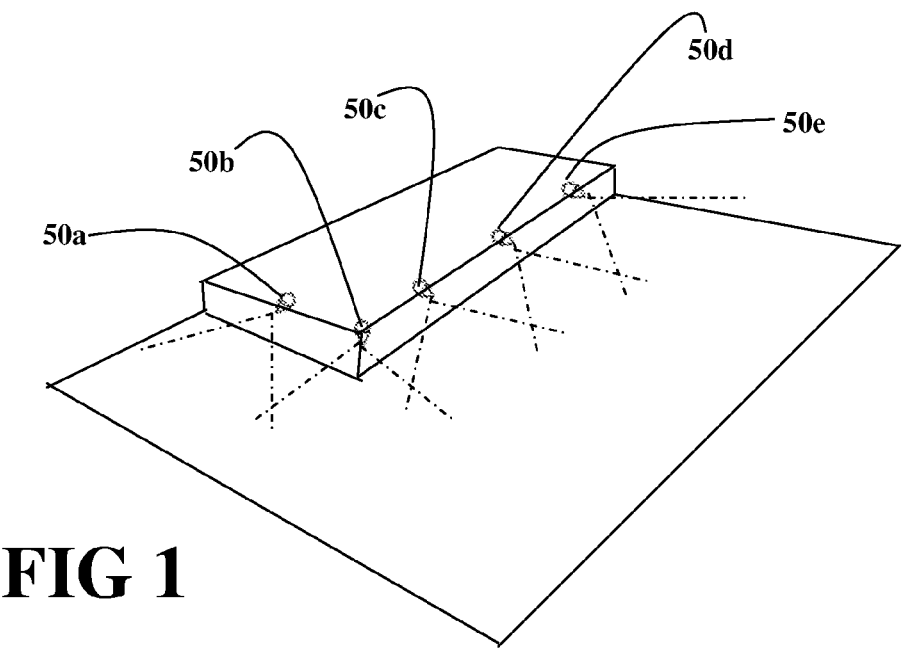
FIG. 1 illustrates a prior art system.
Figure 2:
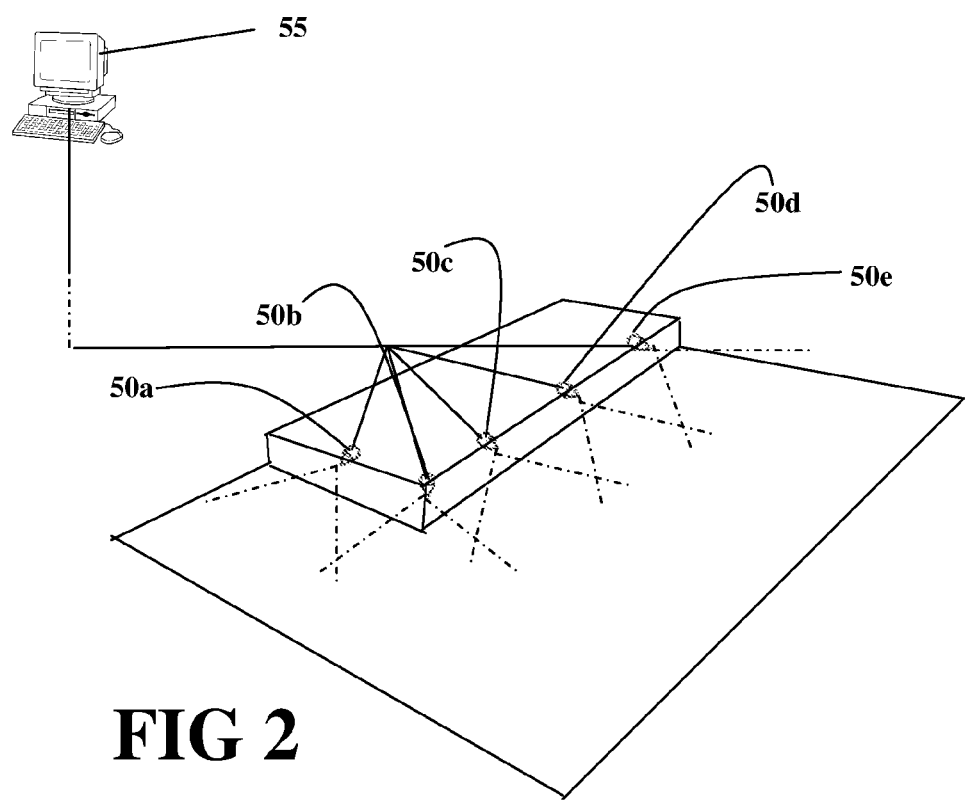
FIG. 2 illustrates an embodiment of the system of the present invention.

According to one implementation, the present invention relates to a system comprising one or more video cameras, such as standard security cameras (e.g. standard security video cameras). FIG. 2 illustrates an embodiment of the invention, wherein a series of cameras (50a-50e) are placed on top of a building aiming at covering the surrounding of a building (e.g. a warehouse building). Each camera covers a certain field of view adjacent to the adjacent camera's field of view. Security personnel can view the cameras filming recordings at a remote location. The system enables tracking capabilities and allows security personnel to mark a subject on the camera viewing screen for tracking said subject, using appropriate tracking applications such as "Six Sense" by NESS technologies, or such as MATLAB tracking application.

The one or more cameras 50a-50e are connected to (or wirelessly in connection with) processing means 55 such as a standard computer. The processing means 55 are adapted to take a plurality of sequential video frame images ("video frames" or just "frames" used herein interchangeably) of a subject and to analyze a specific region of its surrounding in the frequency domain. The region in the frequency domain is then marked with a signature (representing the subject) and stored in a database. The system provides the ability such that when the subject enters the field of view of another camera, or disappears and returns to the same camera field of view, the subject new surrounding is analyzed, (optionally signatured) and compared with the system signature database. The system matches between the new measured properties and the signatures stored in the database. If the coherence between the compared items is above a certain threshold (i.e. matching items) then the identification is deemed positive, thus determining that the subject represented by the currently obtained analysis is the subject represented by the matching signature. Thus system personnel are informed of the positive identification.

According to a preferred embodiment of the present invention, the analysis of the frames method and the signature are implemented according to one or more of the following:

Obtaining the Background of the Frames

A plurality of sequential digital image frames 10 are extracted from a digital video of a system filming recording camera and are saved in a system database and are analyzed/processed by the processing means 55 (e.g. a processor interactive with a memory and configured to carry out functions of various function modules) coupled thereto. The frames extracted typically comprise a moving subject person. At least some of the frames 10 comprise at least portions of the moving person. The frames comprise a foreground which relates to the moving objects within the image such as the moving person, and a background at the areas which are not part of the moving objects foreground. The number of the plurality of frames 10 is usually between 4 and 100 frames.

It should be noted that the present invention is especially useful with a surveillance video camera and the frames are extracted when the camera is active in a still position such that the general background regions location in the frames (the portions without the moving subject person) remain similar. However, it should be noted that the present invention may be used with a still camera or a movable camera and with sequences of a moving camera as well.

As a first part of the processing, each one of the plurality of frames 10 is processed such that three sets of frames (two additional sets) are obtained for further processing:

(1) A frame without the moving object, being background frame 15 (or 15').

(2) A set of frames with only the moving object being foreground frames 20 (or 20').

(3) A set of frames with the moving object (foreground) and the background—10 (typically the original extracted frames 10 or frames corresponding to the original frames with possible additional processing that aid future calculations).

According to a preferred embodiment of the present invention, a background frame 15 is found by running the recording video back or forward for a predetermined time, such that a frame 15 will be obtained without (or with a minimal portion of) the moving subject person (either before he enters the camera region or after he exits the camera region). An example for obtaining the background frame comprises the system obtaining a short video portion at a certain time before or after (or towards the beginning or towards end of) the analyzed sequence (e.g. a few seconds before or after the sequence) and subtracting one of the frames from the short video portion from another frame of the short video portion (e.g. subtracting the last frame image from the first frame image of the short video portion). If the result is close to zero (null image) then one of said 2 images in the subtraction process is determined as the background frame 15.

According to another embodiment the background frame 15' is obtained as follows. To assist calculation, the processing means comprise a buffer 11 which transfers each of the 2D-signal frames 10 into a 1-D signal, as shown in FIG. 3A. An illustrative example of the pixels of the 2-D still image frames representation and the 1-D representation can be seen in FIGS. 3B and 3C respectively.

The processing means comprise an image statistics function module 12 (e.g. 2-D median function module), which takes the output frames (from the buffer 11) 1-D signals (representing the frames 10) and performs a median function on them, thus practically removing the moving object features (moving person) from each of the 1-D signals and remaining with the backgrounds of the frames. According to one embodiment, the median function includes finding a median threshold of the intensity values of the pixels of the image references set of frames 10. The signals in the background portions of the frame images are almost identical. After performing the median function, generally, the pixels with intensity values beneath the threshold are considered the background portion. The pixels with intensity values above the threshold are considered the foreground portions (portions with the moving subject person). The pixel areas of the foregrounds of the images frames are assigned with the corresponding other background image values (at corresponding locations). Preferably, in case of RGB images, the intensity is the value of the total amplitude of each pixel.

According to an embodiment of the present invention, the median threshold is the numerical value separating the higher half of a data sample from the lower half. For example, count(n) is the total number of observation items in given data. If n is odd then—

Median (M)=value of ((n+1)/2)th item term.

If n is even then—

Median (M)=value of [((n)/2) th item term+((n)/2+1)th item term]2.

Example

For an Odd Number of Values:

As an example, the sample median for the following set of observations is calculated: 1, 5, 2, 8, 7.

Firstly, the values are sorted: 1, 2, 5, 7, 8.

In this case, the median is 5 since it is the middle observation in the ordered list.

The median is the ((n+1)/2)th item, where n is the number of values. For example, for the list {1, 2, 5, 7, 8}, n is equal to 5, so the median is the ((5+1)/2)th item.

median=(6/2)th item
median=3rd item
median=5

For an Even Number of Values:

As an example, the sample median for the following set of observations are calculated: 1, 6, 2, 8, 7, 2.

Firstly, the values are sorted: 1, 2, 2, 6, 7, 8.

In this case, the arithmetic mean of the two middlemost terms is (2+6)/2=4. Therefore, the median is 4 since it is the arithmetic mean of the middle observations in the ordered list.

We also use this formula MEDIAN={(n+1)/2}th item. n=number of values

As above example 1, 2, 2, 6, 7, 8; n=6; Median={(6+1)/2}th item=3.5th item. In this case, the median is average of the 3rd number and the next one (the fourth number). The median is (2+6)/2 which is 4.

If A is a matrix, median(A) treats the columns of A as vectors, returning a row vector of median values.

The still background image outputted from the image statistics buffer 12 is transferred to a reshaping module 13 along with the original image size of the frames 10 thus re-producing a complete 2-D background frame 15'.

Obtaining the Foreground of the Frames

Figure 4A:
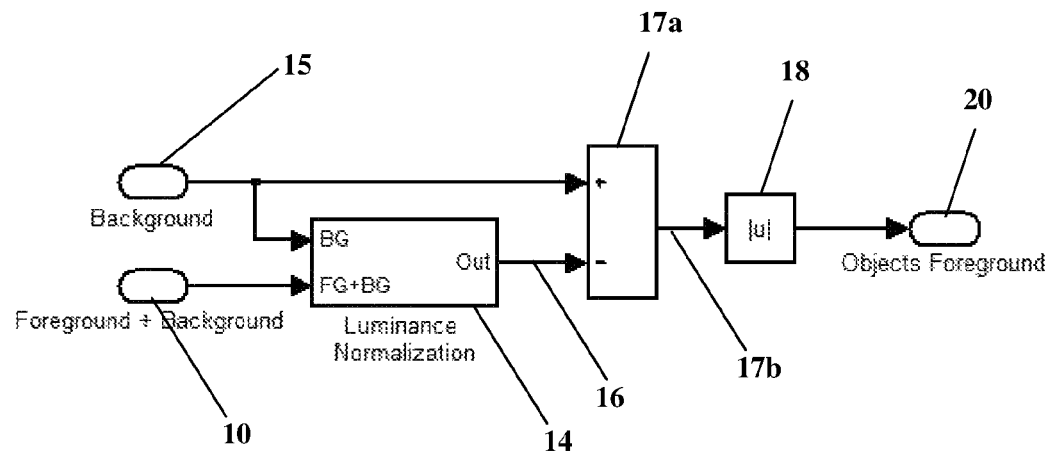
FIGS. 4A-4B illustrate method steps to obtain foreground frames according to an embodiment of the present invention.

A luminance normalization is applied to the original frames such that the frames 10 luminance is adjusted to the luminance of the background frame 15 (or 15', for simplicity we will refer only to 15), as shown in FIG. 4A. The processing means comprise a luminance normalization module 14 which is adapted to change the luminance of one input image to that of another input image. The original frames 10 and the background frame 15 are transferred to the luminance normalization module 14, which adjusts the luminance of each of the original frames 10 to that of the background frame 15. Each luminesced output frame 16 of the luminance normalization module 14 is subtracted from the background frame 15 by a subtracting module 17a. The processing means comprise an absolute value function module which produces the absolute value of an input image frame. The result of the subtraction 17b (the output of subtracting module 17a) is transferred to the absolute value function module 18 and produces the absolute value of subtraction 17b. Consequently, corresponding object foreground frames 20 (outputted from absolute value function module 18) are obtained comprising the objects (e.g. moving people) of the original image.

Figure 4B:
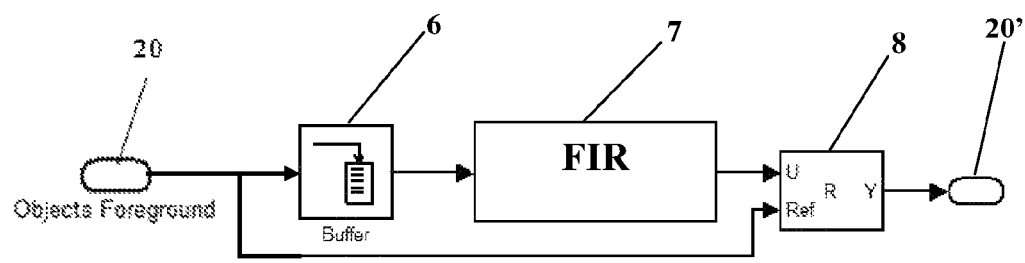

Optionally, an improved object foreground frames 20' can be obtained comprising improved objects (e.g. moving people) of the original image, as shown in FIG. 4B. The object foreground frames 20 are transferred to buffer 6 which transfers them into a 1-D signal (similar to the buffer 11 function). The 1-D signals are transferred to FIR filter 7 which further filters noises of background portions. The mathematics filter implementation is like a classic FIR convolution filter:

$$y(k) = \sum_n u(n-k) * h(k)$$

Wherein y—is the output signal, u is the input signal, h is the filter (array of coefficients, such as a Sobel operator filter), k is the filter element (of the array of coefficients), and n is an index number of a pixel. k and n are incremented by 1.

The filtered frames are then transferred to a reshaping module 8 along with the frame size of frames 20 thus re-producing a complete 2-D improved foreground frames 20'.

FIGS. 4C and 4D show an example of an image 120 before the filtering, and of the image 120' after the filtering. It is clear that background portions (e.g. ground portion 110) that appear in FIG. 4C do not appear in FIG. 4D.

Obtaining the Body Portions of the Foreground Objects

The next stage comprises obtaining the body portions of a person object in the frames. Obtaining the body portion can be done by known functions in the art. One manner of obtaining the body portion is using suitable filters/templates such as Wavelet templates to be applied on the image. Optionally, an average of a group of Wavelet templates can be used.

Figure 5:
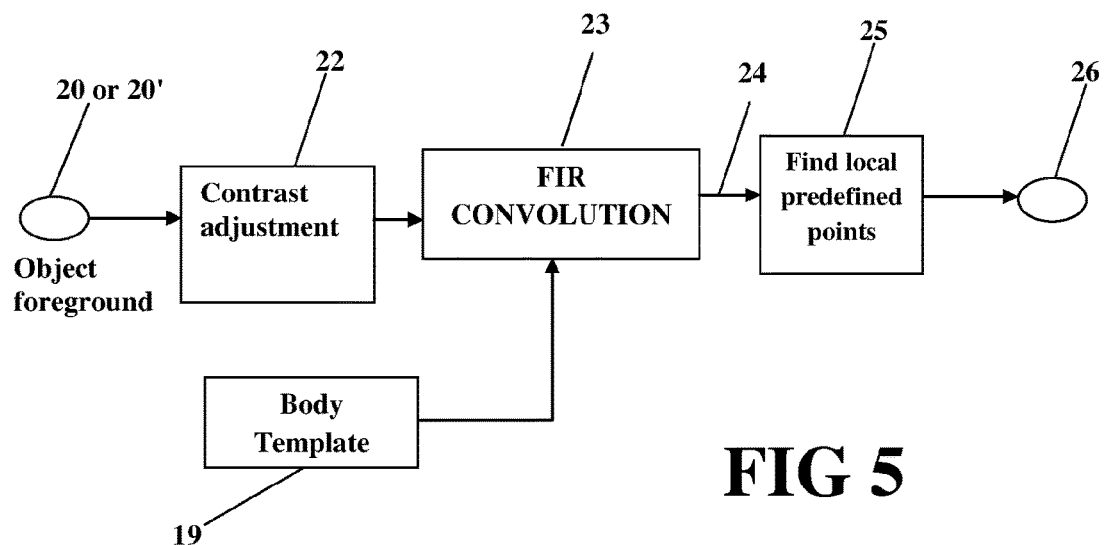
FIG. 5 illustrates method steps to obtain reference point frames according to an embodiment of the present invention.

The processing means comprise a contrast adjusting module which adjusts the contrast of an image such that it becomes optimal as known in the art (shown in FIG. 5). The Contrast Adjustment module 22 adjusts the contrast of an image by linearly scaling the pixel values between upper and lower limits. Pixel intensity values that are above or below this range are saturated to the upper or lower limit value, respectively. The contrast adjustment module provides the system with improved identification results.

The foreground frames (20 or 20') are preferably transferred to the contrast adjusting module 22 (comprised in the processing means) which optimizes the frames contrast.

A wavelet template is used in the method for obtaining body portions within the images. The output of the contrast adjusting is transferred to a FIR convolution module 23 comprised in the processing means. The FIR convolution module 23 convolves the contrast adjusted frames with a selected Wavelet body portion template 19 (or other filter template) in a FIR manner (similarly as explained hereinabove) producing corresponding frames 24 each having an additional coefficients matrix dimension, wherein each frame pixel has a corresponding coefficient of said matrix.

The mathematics filter implementation is like classic FIR convolution-decimation filters:

$$y(k) = \sum_n u(n-k) * h(k)$$

Wherein y—is the output signal, u—input signal, h—is the filter coefficients, k, n—indexes where the index k is incremented by 1, and index n—is incremented by Decimation factor, which is changing from 1 to 2^(Wavelet Levels Number).

The portions of the image with high coefficients (in the additional coefficients matrix dimension) are the body portions (having a body shape) of the foreground objects. The high coefficients are produced due to the compliance of the foreground image body portions and the template 19 characteristics.

Obtaining Direction Vectors

A Local pre-defined points function module 25 (comprised in the processing means) applies a function on the obtained convolved output frames 24 (output of module 23) to obtain corresponding frames 26 with three reference points on each frame. One reference point on each frame is located at the corresponding location to that of the head of the foreground image body portion (preferably top of head). The second reference point on each frame is located at the corresponding location to that of the center of the body of the foreground image body portion. The third reference point on each frame is located at the corresponding location to that of the bottom of the feet of the foreground image body portion. The function that locates these three points is based on Blob Analysis or other similar image processing methods. In cases where frames have only portions of the body (e.g. only head and center body or only feet, etc.) then only the existing corresponding points will be further analyzed.

Figure 6:
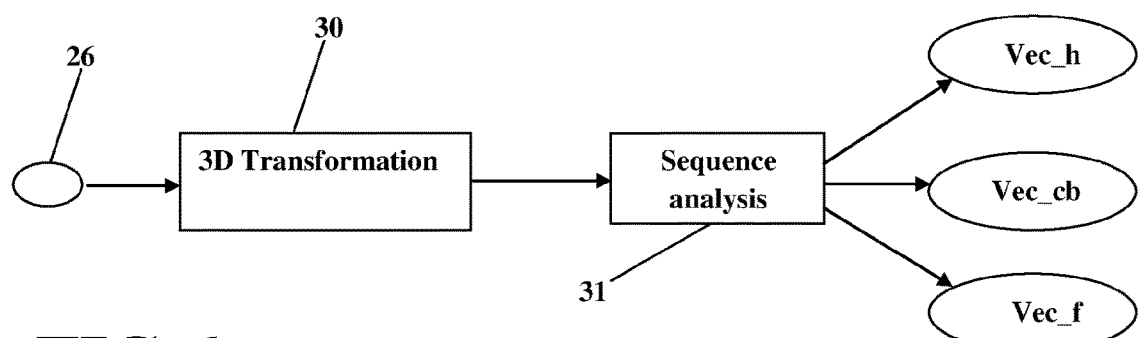
FIG. 6 illustrates method steps to obtain vectors according to an embodiment of the present invention.

The processing means comprise a 3D transformation module 30. The reference points on each of the frames 26 in the sequence are transferred to a 3D transformation module 30, as shown in FIG. 6. The 3D transformation module 30 combines all the reference points frames 26 into a three-dimensional coordinate system comprising all the reference points being at their corresponding location on the three-dimensional coordinate system. The three-dimensional coordinate system corresponds to one frame (having the similar frame size as frames 26) with all of the reference points appearing on it at their corresponding 3D location. It should be noted that the sequence order of the reference points is also stored.

A sequence analysis module 31 analyses the plurality of reference points of the "head" reference points on the three-dimensional coordinate system, and searches for a sequence of a predetermined number of "head" reference points (preferably between 4-10) along the whole "head" points sequence, that produces the most stable vector—Vec_h (comprised of the predetermined number of "head" points). Each "head" reference point on the three-dimensional coordinate system has a 3D location (on the x axis, y axis and z axis) and the most stable vector, i.e. the predefined number of sequential "head" reference points that are most linear, are determined to be the most stable vector Vec_h.

The sequence analysis module 31 analyses the plurality of reference points of the "body center" reference points in the same manner mutatis mutandis producing the most optimal center body vector Vec_cb. The 3D transformation module 30 analyses the plurality of reference points of the "feet" reference points in the same manner mutatis mutandis producing the most optimal feet vector Vec_f.

Obtaining ROIs

Certain areas near the vectors (when integrated in certain frames) are obtained for spectrum analysis, herein referred to as ROIs (regions of interest). These ROIs are preferably on surfaces near the vectors (e.g. walls, floor, ground) such that the moving subject person has a maximal and selective effect on the spectral frequency response (and with minimal noise) at the ROI locations. The dispersing of the spectrum of the light energy measured there is clear and specific (sharp and not smeared) and all this in relation to a location where the subject person is not present. The ROIs are determined according to the optimal light reflex and best resolution in the frequency band. Thus the ROIs are spectrally analyzed.

According to one embodiment of the present invention, a sequence plurality of background frames 10bg are obtained by a short video portion at a certain time before or after (or towards the beginning or towards the end of) the analyzed sequence frames 10 (e.g. a few seconds before or after the sequence). For determining them as background frames, for example, each frame of the potential background frames in the sequence is subtracted from one specific background frame of the sequence (e.g. the most middle one). If the subtraction result is close to zero (null image, up to a certain level) for each subtraction then that sequence of frames is indeed determined as a background frames 10bg sequence. Otherwise, another sequence is checked (e.g. a few seconds before/after), and so on and so forth, until all the frames in the potential background sequence of frames are determined as a background frames 10bg sequence.

Then, the vectors Vec_h, Vec_cb and Vec_f are integrated with the background frame sequence 10bg such that each of the background frames 10bg now comprises a three-dimensional coordinate system, with said vectors at their corresponding locations (i.e. at the same relative areas in the frame e.g. same relative pixels).

The ROIs may be various shapes e.g. squares, rectangles, circles, on the background frames 10bg and various sizes. The ROIs may be found in several manners. Initially, a point on the background frames 10bg being at a predefined distance at 90° (or other predefined angle) from head vector Vec_h center is defined as the center of the ROI. It should be noted that the ROI preferably has a two-dimensional shape but its position is in the three-dimensional coordinate system initially parallel to the head vector Vec_h. Typically the ROI near the head vector Vec_h is most efficient when on a wall. Optionally, 3D known techniques may be used for identifying a wall (or ground) and the distance of the wall from the vector. An appropriate distance of the initial ROI may be determined accordingly.

A transformation function to the frequency domain is applied (e.g. FFT) on the relevant time axis to the initial ROI locations of the background frames 10bg, thus producing the spectral characteristics, e.g. PSD (power spectral density and/or PeakToPeak, PeakToRMS, RMS, etc.) of that ROI indicating its amount of energy. Particularly, the most stable frequencies, i.e. the frequencies which change the least (or do not change at all) over the measured time produced in the transformation function are stored for further analysis.

The initial ROI is integrated with the plurality of sequential digital image frames 10 such that each of the frames 10 now comprises a three-dimensional coordinate system, with said initial ROI at its corresponding locations. The signals (image portions) of each of the frames 10 at the corresponding locations to the initial ROI are obtained. The processor carries out a transformation to the frequency domain (e.g. FFT) function in time to all the signals in the frames 10 corresponding locations to those of the initial ROI thus obtaining spectral characteristics (e.g. PSD) values in the frequency range for the initial ROI.

The present invention comprises an optimization process 40. The optimization process comprises ROIs being integrated with the plurality of sequential digital image frames 10 shifting the ROI along three dimensional axes in predefined increments on all three axes (and combinations thereof). In each shift, the transformation function in time is applied to the ROI currently being checked at its corresponding location in the sequence frames 10. In each shift the sensitivity of the stable frequencies (found in the transformation function of the initial ROI of the background frames 10bg) are evaluated by the processor performing a transformation to frequency domain function (e.g. FFT) in time to all the signals in the frames 10 corresponding locations to those of the ROI being checked thus obtaining spectral characteristics (e.g. PSD) values in the frequency range for the ROI being checked. After checking the sensitivity of the stable (stability) frequencies in all of the potential ROIs (all of the ROIs checked during the shifting process) the ROI with the highest sensitivity (i.e. with the stable frequencies that are mostly changed relative to their characteristics in the background frames 10bg transformation function)—ROI_h, is determined for further analysis. Furthermore, the spectral properties (e.g. PSD) of frames 10bg are calculated by a transformation function in time at regions ROI_h.

An example of the shifting is as follows. The center point of the initial ROI is considered as the center of a three dimensional coordinate system (0,0,0) wherein the head vector Vec_h is parallel to the X axis (e.g. first Cartesian axis), the center of the vector and center (0,0,0) are on the Y axis (e.g. second Cartesian axis) and the perpendicular axis to the X and Y axes (e.g. third Cartesian axis) is the Z axis. The center point of the initial ROI is shifted such that it will pass on all whole points (with whole numbers) of a cuboid having center at (0,0,0) wherein each predefined increment is a whole number. The shifting is carried out according to a shifting rule until all the shifted ROIs according to the rule are evaluated. Other shifting methods as known in the art may also be used such as shifting according to a 3-dimensional Polar coordinate system e.g. varying distance from center of vector Vec_h and varying angles therefrom, etc. Other shifting methods includes semi-random shifting, etc. Optionally, if a sensitivity evaluation of a certain ROI being checked is found to be good (above a certain threshold) then the corresponding ROI may be determined immediately as ROI_h without continuing the rest of the optimization process according to the shifting rule.

Figure 9A:
FIGS. 9A-9B illustrate the vector and ROI on a sequence frame according to an embodiment of the present invention.
Figure 9B:
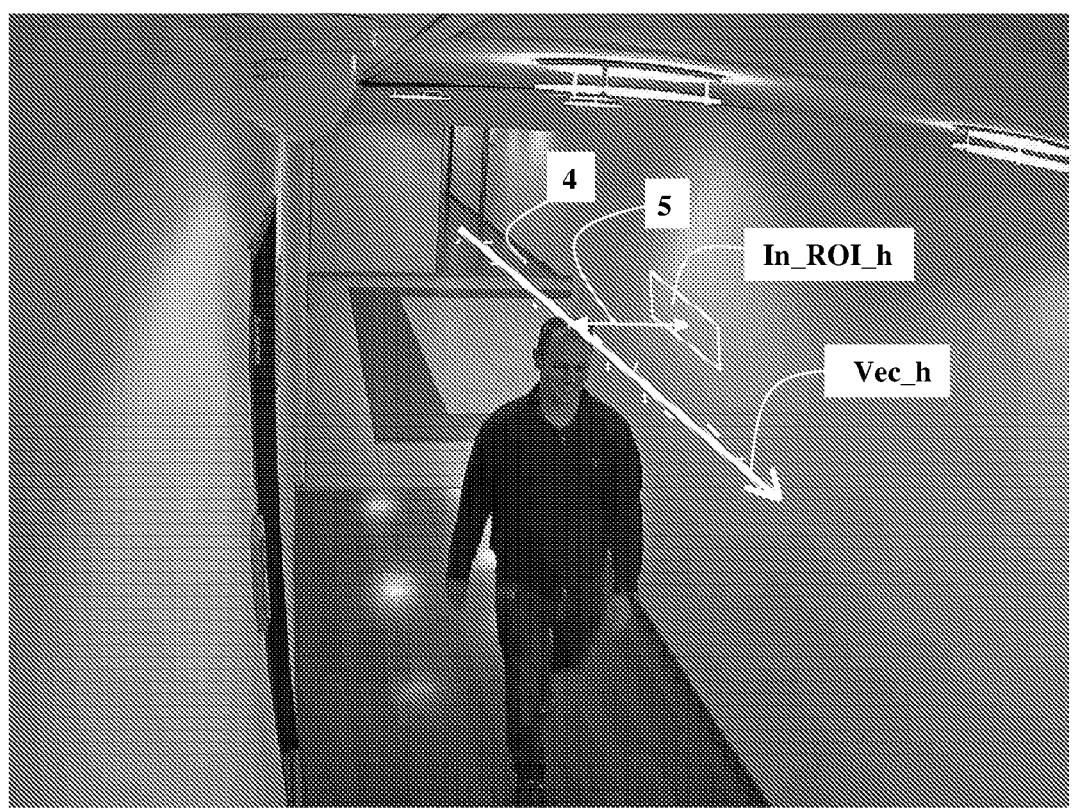

FIGS. 9A-9B show an illustrative example in order to understand the invention more clearly and to obtain a more illustrative feeling of the invention. FIG. 9A illustrates one of the sequence frames 10 comprising a walking person. FIG. 9B illustrates the head vector Vec_h and the initial ROI In_ROI_h (and the distance therebetween 5) integrated in the sequence frame 10 of FIG. 9A. Furthermore, for illustrative purposes the head reference points 4 of all the sequence frames which generate the vector Vec_h are shown along the vector (for illustrative purposes and are not necessarily geometrically exact).

Figure 7:
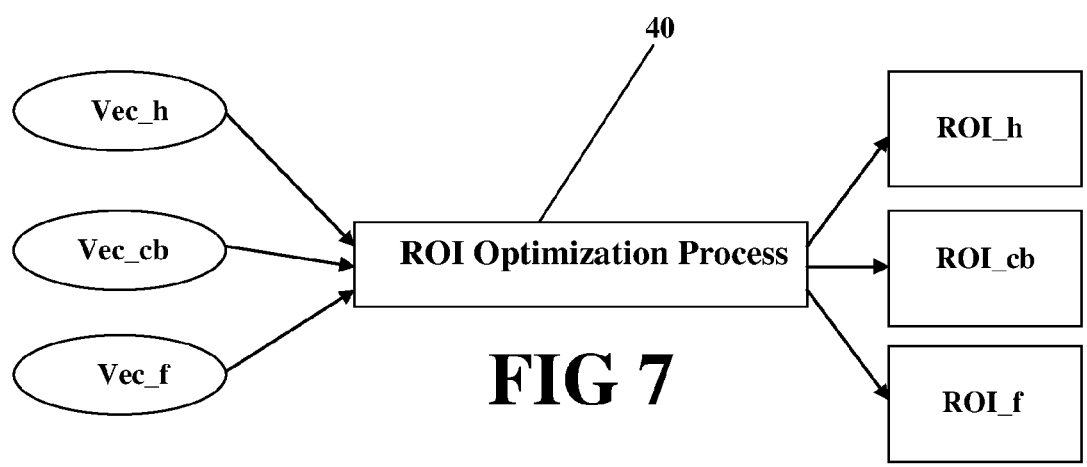
FIG. 7 illustrates method steps to obtain regions Of Interest (ROIs) according to an embodiment of the present invention.

The optimization has been explained hereinabove with relation to the head vector Vec_h determining the ROI with the highest sensitivity ROI_h. Appropriate ROIs with the highest sensitivity are found in relation to vectors Vec_cb and Vec_f after a similar optimization process, in the same manner mutatis mutandis (for simplicity the whole process has not been written again for Vec_cb and Vec_f). Thus the ROIs with the highest sensitivity—ROI_cb (in relation to center body vector Vec_cb) and ROI_f (in relation to feet vector Vec_f) are determined for further analysis (shown in FIG. 7).

Optionally the other sides of the vectors (90° of the other side, or 270°) can also be checked and optimized in a similar manner obtaining the best ROI result of the two sides to be the ROI for further processing.

It should be noted that typically the ROIs near Vec_cb and Vec_f are most efficient when on the floor/ground.

It should be noted that according to one specific embodiment, in cases where a sequence of "pure" background frames are hard to find (e.g. when most appropriate to use the image statistics function module 12 as explained hereinabove e.g. 2-D median function module) a sequence of background frames 10bg are used where the subtraction from one another is minimal (even if not close to zero). According to one embodiment, the ROI is shifted only within the locations that have been found to be background locations during the "Foreground/Background separation process as explained hereinabove (with the image statistics function module 12, 2-D median function module, etc.).

Furthermore, the initial ROI integrated with the plurality of sequential digital image frames 10, may be determined also by an optimization process (and not necessarily by a predefined area in relation to its corresponding vector). According to this embodiment, a first initial ROI is determined according to a predefined area in relation to its corresponding vector. Then the first initial ROI is shifted (in a similar manner according to one of the methods explained hereinavove) and the stable frequencies are measured. The result of the stability of each of the shifted ROIs are evaluated and the one with the highest stability is determined as the (initial) ROI for the subsequent optimization stage according to the sensitivity (in relation to said highest stability). Then the final ROI determined is the one with the highest sensitivity, as explained hereinabove, etc.

Signature

The term "signature", or "signatured" or "signed" (in past tense) refer to saving a frequency factor in the processing means database under a certain name/identification.

The spectral characteristics (e.g. PSD) values in the frequency range for the determined ROI with the highest sensitivity (of the stability frequencies) ROI_h is stored in the system memory/database. This storing is actually part of the signature of the subject person saving his biometric characteristics based on quantum radio physics of the subject person in the system memory/database.

The same thing is carried out in relation to the spectral characteristics (e.g. PSD) values in the frequency range with the highest sensitivity (of the stability frequencies) ROI_cb and ROI_f (near the center body and feet respectively). They are also stored mutatis mutandis.

Optionally, the processor carries out a spatial transformation to frequency range function (e.g. FFT) to one or more of the sequence frames 10 and to one or more of the background frames 10bg at the corresponding ROI_h, ROI_cb and ROI_f locations thus obtaining spectral characteristics (e.g. PSD) values of spatial features at the corresponding ROI_h, ROI_cb and ROI_f locations. According to this option they are also stored as part of the signature. Typically, when carrying out the transformation and saving in the spatial range for only one frame of the sequence frames 10 it can be the middle frame in the sequence. Typically, when carrying out the transformation and saving in the spatial range for only one background frame of the sequence background frames 10bg it can be the middle frame in the sequence.

Figure 8:
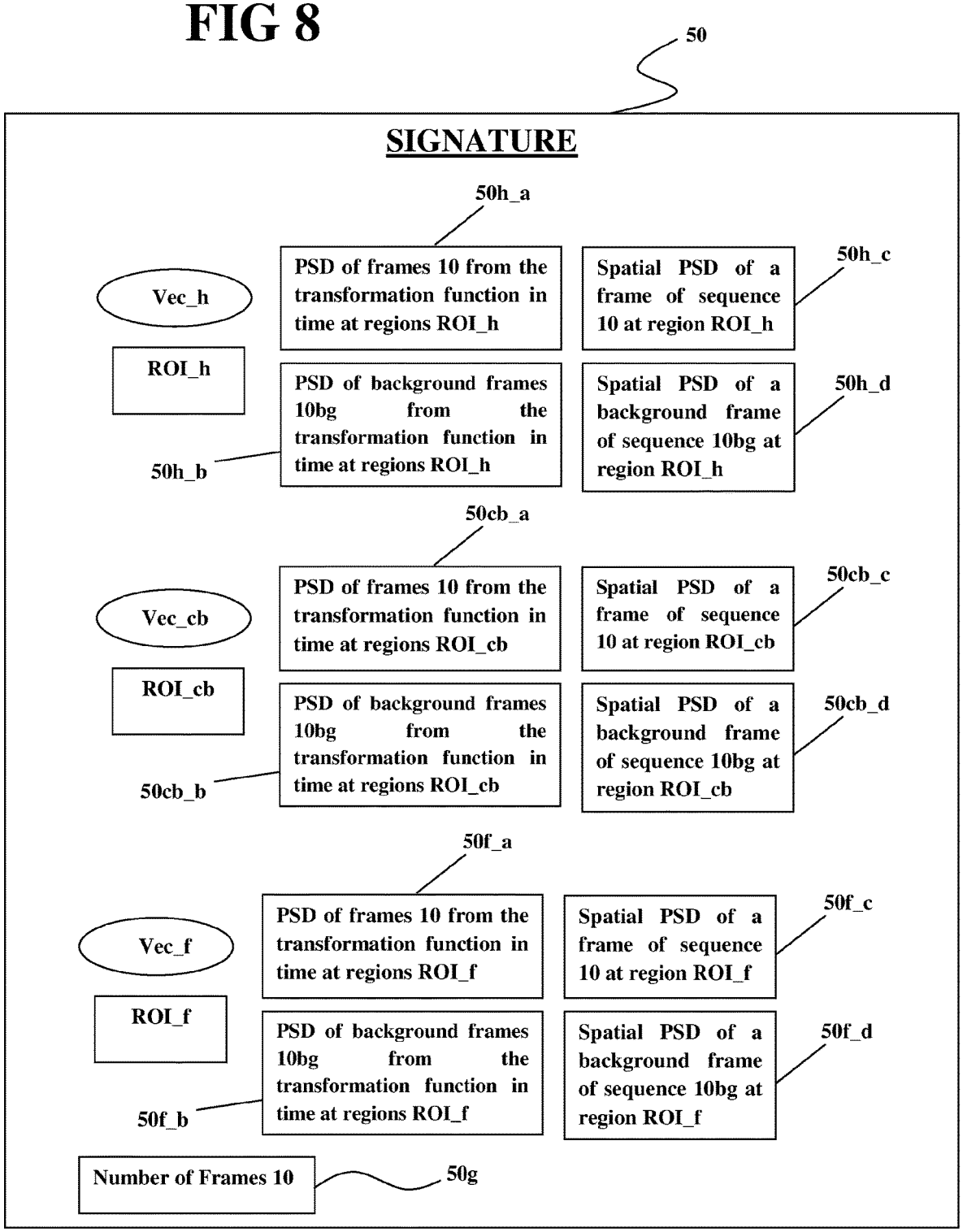
FIG. 8 illustrates an example of a signature according to an embodiment of the present invention.

FIG. 8 shows an embodiment of the present invention—a full signature 50 comprising 12 frequency spectral characteristics (for example the PSD) results stored as representing the subject person. Furthermore, the vectors and optimized ROIs (optimized ROI locations) leading to the spectral characteristics (e.g. PSD) results are also stored as part of the signature. 50h_a indicates the signature of spectral characteristics (for example the PSD) of frames 10 from the transformation function in time at regions ROI_h. 50h_b indicates the signature of the spectral characteristics (e.g. PSD) of background frames 10bg from the transformation function in time at regions ROI_h. 50h c indicates the spatial spectral characteristics (e.g. spatial PSD) of one of the sequence frames (of sequence frames 10) at region ROI_h (which was also calculated by the processor). 50h_d indicates the spatial spectral characteristics (e.g. spatial PSD) of one of the background frames of 10bg at region ROI_h (which was also calculated by the processor). The corresponding region ROI_h and corresponding vector Vec_h are also stored as part of the signature.

50cb_a indicates the signature of spectral characteristics (for example the PSD) of frames 10 from the transformation function in time at regions ROI_cb. 50cb_b indicates the signature of the spectral characteristics (e.g. PSD) of background frames 10bg from the transformation function in time at regions ROI_cb. 50cb_c indicates the spatial spectral characteristics (e.g. spatial PSD) of one of the sequence frames (of sequence frames 10) at region ROI_cb (which was also calculated by the processor). 50cb_d indicates the spatial spectral characteristics (e.g. spatial PSD) of one of the background frames of 10bg at region ROI_cb (which was also calculated by the processor). The corresponding region ROI_cb and corresponding vector Vec_cb are also stored as part of the signature.

50f_a indicates the signature of the PSD of frames 10 from the transformation function in time at regions ROI_f. 50f_b indicates the signature of the spectral characteristics (e.g. PSD) of background frames 10bg from the transformation function in time at regions ROI_f. 50f_c indicates the spatial PSD of one of the sequence frames (of sequence frames 10) at region ROI_f (which was also calculated by the processor). 50f d indicates the spatial spectral characteristics (e.g. spatial PSD) of one of the background frames of 10bg at region ROI_f (which was also calculated by the processor). The corresponding region ROI_f and corresponding vector Vec_f are also stored as part of the signature. For specific applications, the signature may comprise less than 12 sub signatures (e.g. only one, two, three, four or five of the signatures in the signature 50).

Furthermore, the number of frames 50n of frames 10 is stored in the in the signature 50. This is for the purpose of future comparison—when the signature is compared to a presently checked item—the same numbers of frames may be taken for the presently checked item for a better accuracy result of the transformation to frequency range function. The comparison will be explained hereinafter in more detail.

Comparison with New Signature

According to a preferred embodiment, when the system operator wants to compare a currently identified subject person with the signatures stored in the database it is performed as follows. For the new subject person, the method as explained hereinabove is performed until the step of finding the RIOs (not included), i.e. obtaining background, foreground, body portions, vectors, and background sequence (equivalent to 10bg).

A. Geometry Adaptation to Find New ROIs

Then, the ROIs for the new subject person are obtained in relation to the geometry of the currently checked data signature in the database. The new subject person ROIs are positioned in the spatial conditions (in 3D) as close as possible to those of the currently checked signature. The ROIs are chosen at the same distance and spatial angle from the vectors (e.g. from the center of the vectors) as the distance and spatial angle between the signatured angles and distances from their vectors. It should be clear that distance/angle of the head vector of the subject person being checked should be the same as the distance/angle of the head vector in the signature, and the same goes for the center body and feet features, mutatis mutandis. Thus the found ROIs are integrated into the sequence frames being checked (equivalent to sequence 10) and background sequence (equivalent to sequence 10bg).

The distance and spatial angles between the signatured ROIs and the signatured vectors are calculated by the processing means or optionally they could be calculated and stored within each saved signature.

B. Compare Background ROIs and Prediction

Then, a transformation function to the frequency range in time is applied (e.g. FFT) to the background sequence (equivalent to sequence 10bg) of the currently checked subject person—at the new ROIs (adapted according to the signatured geometry), thus producing their spectral characteristics (e.g. PSD) at the ROIs—60h_b, 60cb_b and 60f_b (for head ROI, Center Body ROI and Feet ROI respectively).

Figure 10:
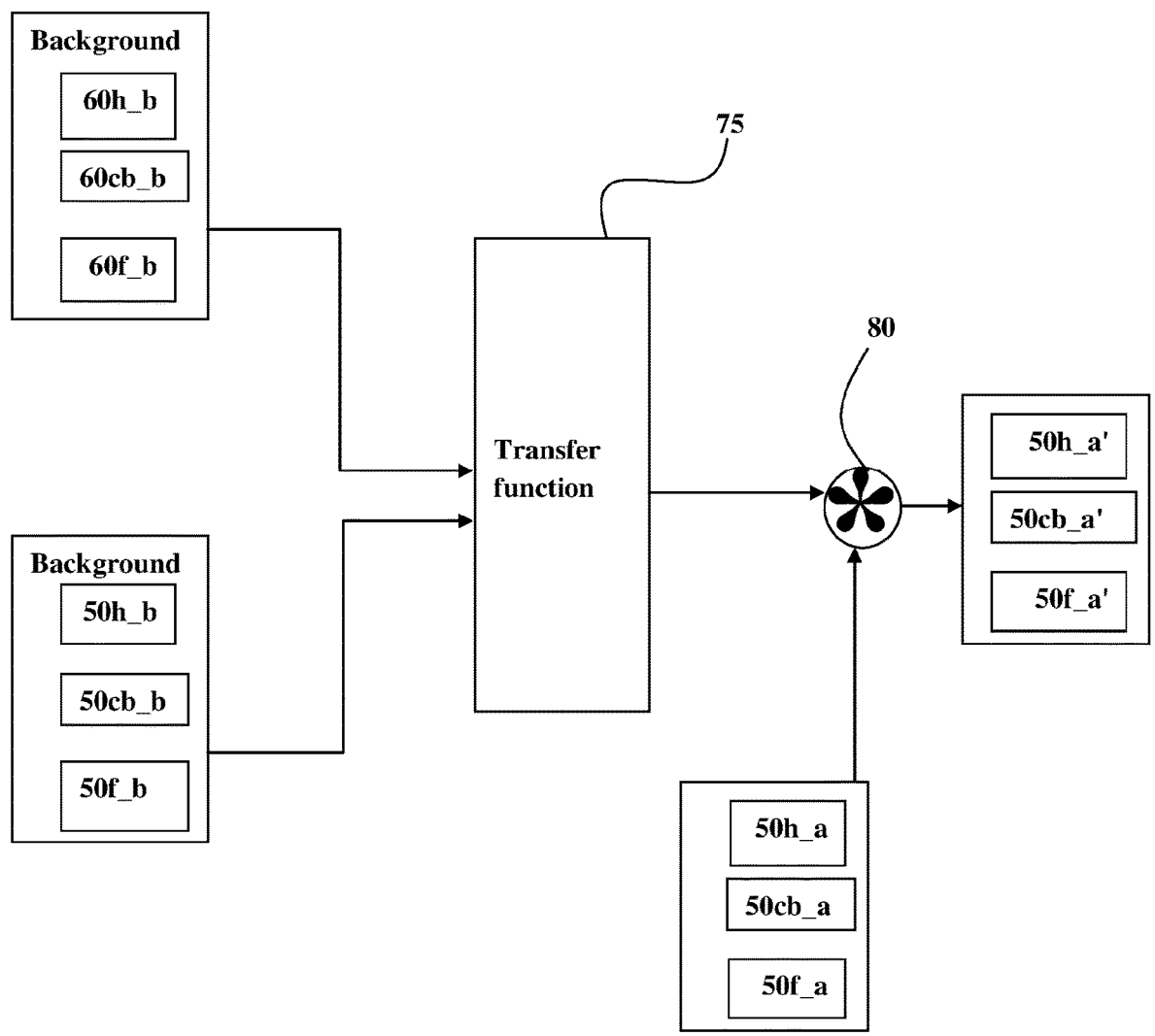
FIG. 10 illustrates a transfer function and shifting according to an embodiment of the present invention.

The results of the background sequence frequency PSDs 60h_b, 60cb_b and 60f_b (relating to head, center body and feet respectively) of the currently checked subject person are inputted into a transfer function module 75 along with the currently checked signature background signatures 50h_b, 50cb_b and 50f_b, as shown in FIG. 10.

The transfer function module 75 evaluates the difference between the values of 60h_b and 50h_b (e.g. multiplication matrix, convolution, Fir filter, etc.). This relative difference is applied by a shifting module 80 shifting the value of the currently checked signature original frames time signature 50h_a (in relation to the head) in a proportional manner (as the difference between 60h_b and 50h b) to obtain a corrected/predicted signature 50h_a'. In the same manner the transfer function module 75 evaluates the difference between the values of 60cb_b and 50cb_b and evaluates the difference between 60f_b and 50f_b. These relative differences are applied by shifting module 80 shifting the value of the currently checked signature original frames time signatures 50cb_a and 50f_a (in relation to the center body and feet respectively) in a proportional manner obtaining corrected/predicted signatures 50cb_a' and 50f_a' (in relation to the center body and feet respectively) in the same manner with the necessary changes.

C. Comparison

Finally, the original sequence frames of the currently checked new subject person are obtained. The processor carries out a transformation to the frequency domain (e.g. FFT) function in time to all the signals in the frames at the new found ROI portions/locations, thus producing their frequency characteristics (e.g. PSDs)—60h_a, 60cb_a and 60f_a (relating to head, center body, feet respectively).

These values are evaluated with the shifted values found of the shifted signatures (50h_a', 50cb_a' and 50f_a') respectively to find the coherence between them. The coherence function of the values being compared produces a result indicating how close the subject persons (of the signature and the currently checked person) effect on the ROIs are, indicating that they are the same person. For example, a positive match (identification) would be if the coherence function would indicate upon an 80% or 90% similarity between the values. A threshold percentage of similarity can be chosen by a system user wherein a percentage above the threshold indicates a positive identification and a percentage below the threshold indicates a negative identification.

Figure 11:
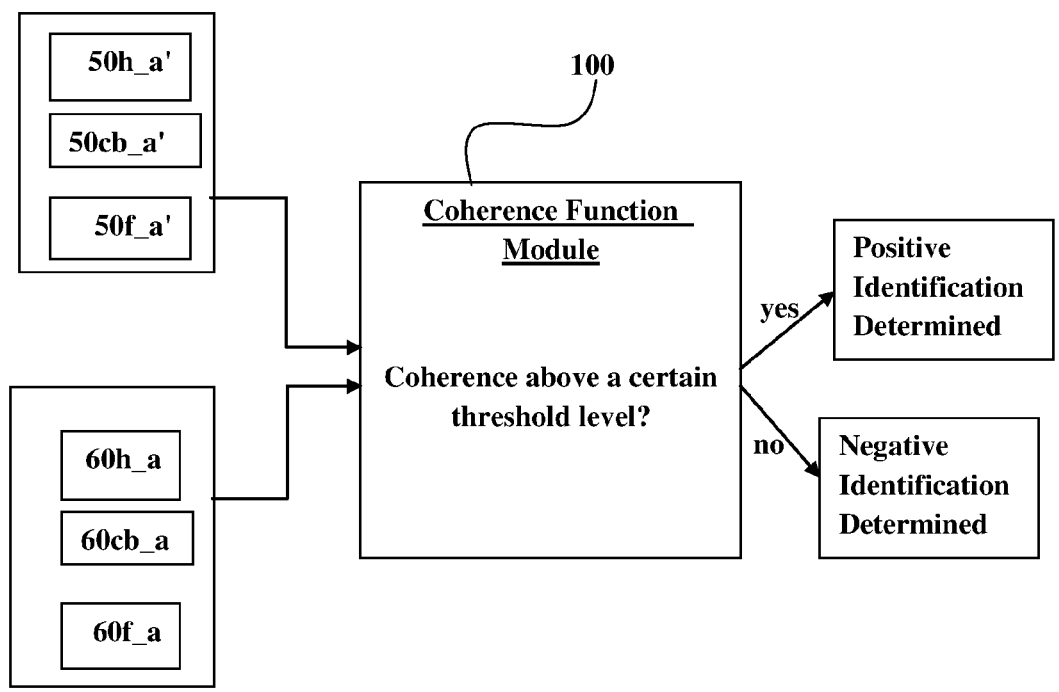
FIG. 11 illustrates a coherence comparison function according to an embodiment of the present invention.

The coherence is compared by a coherence function module 100 (shown in FIG. 11) between the frequency PSDs of 60h_a and 50h_a'. If the coherence level is above a certain threshold then an identification between the currently checked subject person and the signed person (the currently checked signature in the database) is deemed positive. If the coherence level is beneath a certain threshold then an identification between the currently checked subject person and the signed person (the currently checked signature in the database) is deemed negative. A similar comparison is made between the frequency PSDs of 60cb_a and 50cb-_ab' and between 60f_a and 50f_a', mutatis mutandis.

A positive identification can be determined with only one of the three (head, center body, feet) comparisons being positive or with two being positive or optionally with all three being positive.

A similar determination may be made with the spatial frequency spectral characteristics of the signatured subject and the currently checked subject, wherein the adaptation is according to the spatial background signature frame 50h_d, (and 50cb_d and 50f_d and also using 50h_c, 50cb_c and 50f_c), mutatis mutandis.

It should be clear that the present invention preferably comprises, when comparing the features of two subjects, that the adaptation and shifting (ROIs and vectors) for the comparison can be carried out from the first to the second and from the second to the first. This is true especially when comparing two signatures, the operator may choose adapting the geometry features of a desired signature to those of the other or vice versa.

However, the present invention also comprises comparison between spectral characteristics which one has not necessarily been adapted to the other (e.g. by transfer function). The coherence is evaluated and an identification is determined. Therefore, two signatures may be compared in the coherence function module even without the same number of sequence frames or same relation between ROI and vector. The spectral characteristics are just compared and a determination can be made. Naturally, the same amount of frames and corresponding ROIs in relation to the vectors may contribute to effectiveness of the comparison.

Figure 12:
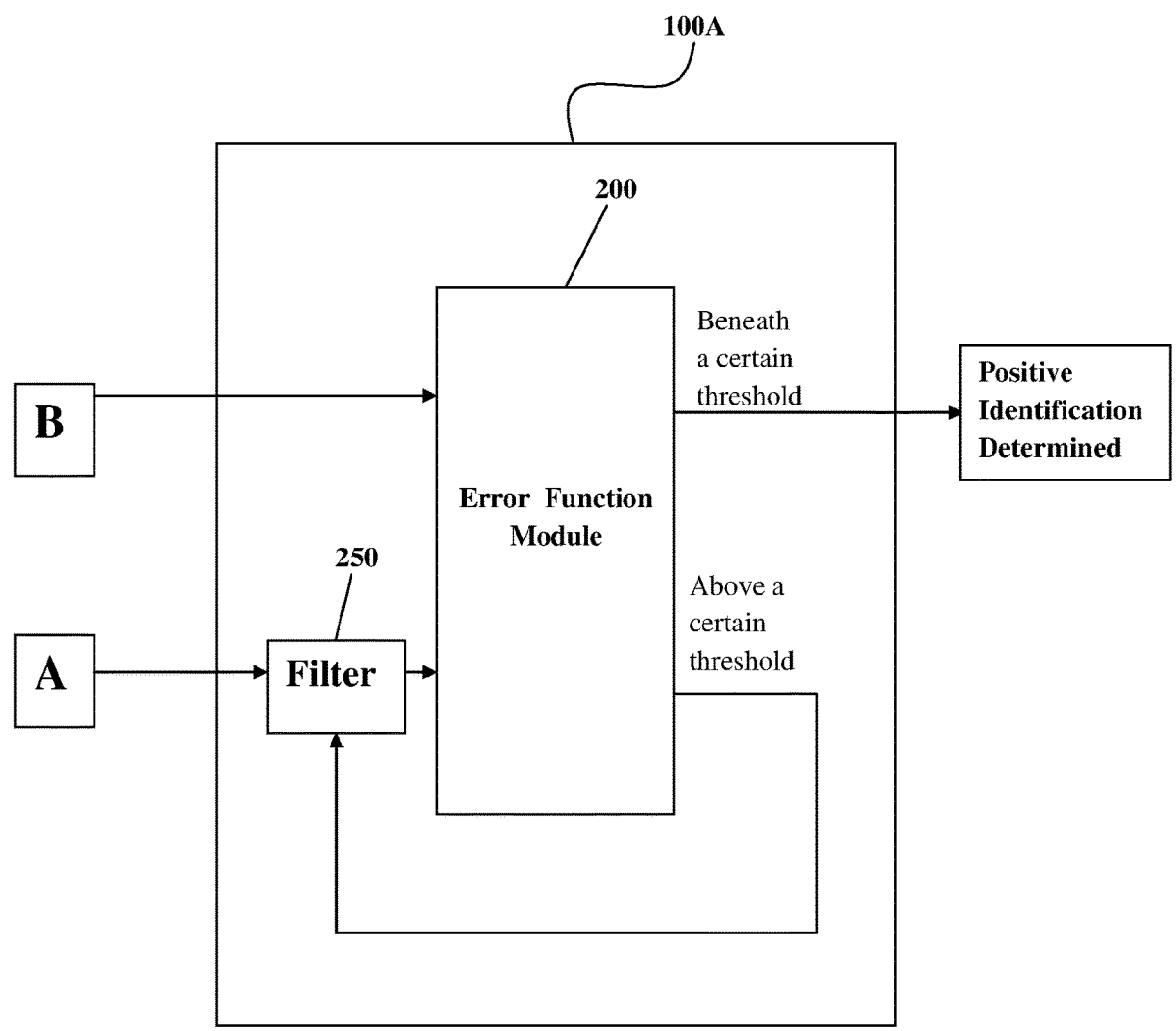
FIG. 12 illustrates a coherence comparison function with filter according to an embodiment of the present invention.

FIG. 12 illustrates an example of a coherence function module 100A. Two frequency spectral characteristics (e.g. PSDs) A and B (e.g. two signatures in a database, or (1) a currently determined (according to the present invention method) spectral characteristics and (2) a signature in a database) as explained hereinabove are inputted into the coherence function module 100A.

The coherence function module 100A comprises an error function module 200 that obtains the error between the inputted two frequency spectral characteristics (e.g. subtracts one of the initial inputted frequency spectral characteristics from the other initial one). If the error between them is beneath a certain threshold—then a positive identification is determined between the persons of the frequency spectral characteristics of A and B. If the error between them is above a certain threshold then the error is transferred to an adaptive filter 250 (e.g. BSS, LMS, RMS, other convergent evaluation modules) that adapts the values of spectral characteristics A according to the error level (e.g. adapts the coefficients of the filter according to the error output level). The adapted spectral characteristics is inputted into the error function module 200 that subtracts adapted A from B. If the error between them is beneath a certain threshold—then a positive identification is determined between the persons of the frequency spectral characteristics of A and B. If the error between them is above a certain threshold then the error is transferred to adaptive filter 250 that adapts the values of spectral characteristics A according to the error, and so on and so forth.

If the loop continues a number of times above a predetermined threshold then the final determination of the identification between A and B is deemed negative. If the loop continues a number of times beneath the predetermined threshold then it means that at some point the error calculated is beneath a certain threshold and the loop is broken thus determining a positive identification.

The comparison may be made between time or spatial spectral characteristics as described hereinabove. Optionally, the first time the spectral characteristics of A is fed to the error function module 200 the adaptive filter 250 may adapt it according to a predefined adapting function. Optionally the first time A is fed to the error function module 200—A is not adapted at all.

Optionally, the time of the convergence may be the threshold factor to a positive identification or not, i.e. if the loop breaks before a predetermined threshold time the identification is deemed positive. Optionally, when given 2 signatures and it is wanted to check which of them corresponds to a third signature, a possible manner of determining a positive determination is which of the two being compared to the third signature with the corresponding error therebetween being converged in a faster manner.

The present invention system is adaptive, i.e. it can take multiple video samples of a certain subject surrounding and corrects its signature features according to the feedback received from the later video samples. This improves the coherence (and credibility/reliability) of the signature. The final signature can be an average of the frequency properties of a few samples of the subject person.

According to an embodiment of the present invention, various types of machine learning methods may be used for classification of the saved signatures.

The present invention can be used to efficiently and quickly search for a specific person in a video, on-line or during a post event analysis. For example, if security forces have a video sequence of a wanted suspicious subject, they can obtain his surrounding ROIs frequency features according to the present invention and compare with other subjects (in video camera films) surrounding ROI frequency features (optionally pre-signing them too) or with signatures saved in a database, to receive a positive/negative identification determination.

The present invention enables personnel to mark a moving subject person on a video for analyzing and signature as explained hereinabove and also enables an automatic marking, analysis and signature of subjects entering a field of view (e.g. using appropriate tracking applications) and automatic comparison with the database. For example, if there is a wanted suspicious subject and his signature is saved in a database, the automatic feature may obtain the surrounding ROIs frequency features of each person entering a field of view of the cameras of the system and (optionally sign and) adapt and compare them to the signature of the wanted suspicious subject.

Tracking

When a suspicious subject enters one of the system cameras field of view security personnel can mark the suspicious subject on the viewing screen causing the operation of a tracking system (or a subject can be tracked automatically). The tracking system application is an application software generally on the same processing means that enables marking a subject (with a computer mouse or with touch screen, or automatically by motion detection software etc.).

The present invention also enables continuous tracking of a subject moving through adjacent cameras fields of view. First the subject is tracked within the first camera field of view. While in the first camera field of view, the subject may be tracked by carrying out a signature to a sequence of frames and to a consecutive sequence of frames after a predefined time. The most newly-currently frames sequence being signed have their ROIs/vectors geometry adapted to those of the previously signed frame sequence signed (or one of the previous ones) and the positive/negative identification is determined. If the identification is positive the tracking continues.

Preferably, a full signature with a full optimization of ROIs is carried out for the most newly-currently frames sequence being signed, even though for the comparison/determination its ROIs/vectors geometry have been adapted to those of the previously compared signature.

If the identification is negative the tracking ceases. Preferably, the tracking does not cease, but subsequent sequence videos from cameras with adjacent fields of view are analyzed (compared with the last signature in the field of view) to find the subject and continue the tracking if identification is deemed positive. The present invention is advantageous as it allows continuous tracking from one camera field of view to another, as the frequency data is analyzed in a central processing means regardless of a specific camera field of view. The present invention thus enables camera to camera re-identification and complete handshaking (as the sequences evaluated are deemed to be positive i.e. of the same subject person) for continuous tracking. Also the tracking may be along multi-cameras and multi-platforms with the recognition seamlessly across zones.

The present invention may distinguish between multiple people in the field of view, multiple foregrounds by using appropriate distinguishing applications such as Blind Source Separation (BSS) or such as Adaptive Beam Forming.

When the tracked person exits the camera field of view and then returns to it (or to any system camera field of view), the tracking can resume optionally indicating that the person has returned and is once again being tracked. For this option sequences of system cameras are analyzed every predefined time after the subject leaves the field of view.

Uses

Thus the present invention is very useful for use with mounted/mobile cameras with no special mounting required. The present invention has low sensitivity for uneven lighting due to the luminance correction feature, general frequency analysis and shifting feature. The present invention does not require a facial view or hair view.

There is no dependency on clothes, external appearance, change of wear or movement direction/orientation—the frequency analysis on the surrounding ROIs of a moving person are clearly not substantially affected by these changes. The present invention can perform a 360° detection with no need for a specific position towards the camera. Tagging anybody can be carried out anywhere. The signature can be made indoor or outdoor. The identification can be made close to real time and without the cooperation of a subject person. The present invention is especially efficient because several times a subject in a video is unidentifiable. The surrounding ROI frequency features can enable a positive identification.

The present invention is useful for a variety of applications. The present invention can be used for homeland security and intelligence industries with a near real-time video analytics solution identifying suspects based on biometric ID.

The present invention may be used for personalized retailing (commercial analysis) identifying previous customers and linking them with their stored preferences for commercial use (e.g. identifying the same shopper at the cash register and analyzing his purchases), or connecting shoppers to a specific track through different shop departments, etc. The present invention may be used for Commercial Security and industrial/healthcare facilities Safety. The present invention may provide video content management with structured repositories of video content in a searchable, intelligent manner, possibly being accessible to the public.

While some of the embodiments of the invention have been described by way of illustration, it will be apparent that the invention can be carried into practice with many modifications, variations and adaptations, and with the use of numerous equivalents or alternative solutions that are within the scope of a person skilled in the art, without departing from the spirit of the invention, or the scope of the claims.

The invention claimed is:

1. A method for generating a biometric signature of a subject comprising:
obtaining a plurality of sequential video frame images of a moving subject from a video segment;
obtaining a portion of each frame comprising a surrounding of the moving subject;
wherein obtaining the portion of each frame comprising the surrounding of the moving subject comprises:
obtaining foreground frames corresponding to the plurality of sequential video frames, each comprising the moving subject;
generating a vector representing the direction of the moving subject;
determining a Region Of Interest (ROI) at a position in relation to said vector;
wherein determining the Region Of Interest (ROI) at a position in relation to said vector comprises:
a. obtaining a plurality of background sequential video frames being a sequence of frames comprising the background of the plurality of sequential video frame images;
b. integrating the vector determined in each background frame;

c. determining an initial ROI on each background frame being at a predetermined corresponding position from said vector;
d. carrying out a transformation function to the frequency domain in time to the ROI portions of said background frames obtaining spectral characteristics and determining the stability frequencies from said spectral characteristics;
e. integrating each of the plurality of sequential video frame images with said initial ROI determined and carrying out a transformation function to the frequency domain in time to the initial ROI portion of said sequential video frames thus obtaining spectral characteristics and storing the sensitivity of said stability frequencies of said spectral characteristics of the initial ROI;
f. shifting the initial ROI to a surrounding area in each of the plurality of sequential video frame images, and carrying out a transformation function to the frequency domain in time to the currently shifted ROI portion of said sequential video frames thus obtaining spectral characteristics and storing the sensitivity of said stability frequencies of said spectral characteristics of the currently shifted ROI;
g. repeating the shifting step f for all sequences according to a predetermined shifting rule;
h. after step f has been repeated for all sequences of the shifting rule determining the ROI of the initial and shifted ROIs with the highest sensitivity stored as the ROI; and determining said portion of each frame comprising the surrounding of the moving subject, at a location on each frame corresponding to the location of said determined ROI;

carrying out a transformation function to the frequency domain on one or more of said portions of the frames comprising the surrounding of the moving subject; and
saving said spectral characteristics of said transformation function in a repository.

2. The method according to claim 1, wherein obtaining foreground frames corresponding to the plurality of sequential video frames comprises:
obtaining a background frame comprising the background of the plurality of sequential video frame images;
subtracting said background frame from each of the plurality of sequential video frames.

3. The method according to claim 1, wherein generating the vector representing the direction of the moving subject comprises:
obtaining body portions of the foreground objects of the foreground frames;
obtaining reference point frames corresponding to the foreground frames, each comprising a reference point about or at an edge of the corresponding location of said body portions;
combining all the reference points frames into a three-dimensional coordinate system frame comprising all the reference points being at their corresponding location on the three-dimensional coordinate system frame;
determining a vector in the three-dimensional coordinate system frame according to a sequence of a number of reference points from the reference points, that produce the most stable vector.

4. The method according to claim 3, wherein the body portions are one or more of:
a head portion;
a center body portion; or
a feet portion.

5. The method according to claim 1 further comprising a step of identification by comparing the obtained spectral characteristics of the transformation function with spectral characteristics saved in a database, wherein an identification result is deemed to be positive when the coherence level between both compared frequency spectral characteristics is above a certain threshold.

6. The method according to claim 1 comprising performing a signature for a subject by obtaining and saving the vector generated and the corresponding ROI portion determined, and further obtaining and saving one or more of the following items in a database in relation to said subject:
one or more characteristics of a transformation function to the frequency domain in time to the ROI portions of the sequential frames;
one or more spectral characteristics of a transformation function to the frequency domain in time to the ROI portions of the background frames;
one or more spatial spectral characteristics of a transformation function to the frequency domain at the ROI portion of one of the sequential frames; or
one or more spatial spectral characteristics of a transformation function to the frequency domain at the ROI portion of one of the background frames.

7. The method according to claim 1, further comprising a step of identification, comprising:
providing a given biometric signature of a subject person stored in a data base comprising a vector, an ROI, spectral characteristics of a transformation function to the frequency domain in time of a frame sequence, spectral characteristics of a transformation function to the frequency domain in time of background frames;
wherein the Region Of Interest (ROI) at a position in relation to the vector is determined such that it is in the same position in relation to the vector as the signature ROI in relation to the signature vector;
wherein said method further comprises:
i. obtaining the spectral characteristics of a transformation function to the frequency domain in time to the ROI portions of the background frames;
ii. obtaining a relative difference by inputting the spectral characteristics of a transformation function to the frequency domain in time of the background frames of step (i) and said signature spectral characteristics of a transformation function to the frequency domain in time of background frames, into a transfer function;
iii. obtaining the spectral characteristics of a transformation function to the frequency domain in time to the ROI portions of the sequence frames and shifting the value of said spectral characteristics of a transformation function to the frequency domain in time to the ROI portions of the sequence frames, in a proportional manner as said relative difference; and
iv. comparing the shifted values to the signature spectral characteristics of a transformation function to the frequency domain in time of a frame sequence;
wherein an identification result is deemed to be positive when the coherence level between the compared spectral characteristics of step (iv) is above a predefined threshold.

8. The method according to claim 1 further comprising an identification, said method further comprising:
obtaining an error value between the spectral characteristics of the transformation function and spectral characteristics saved in a database;
wherein an identification is deemed positive if one of the following conditions are met:
I) the error value is beneath a predefined threshold value;
II) the following consecutive steps are carried out less times than a predetermined threshold number:
i. transferring the error value to an adaptive filter that adapts the values of one of the spectral characteristics according to the error value;
ii. obtaining an error value between the adapted spectral characteristics value and the other spectral characteristics;
iii. determining if the error value of step (ii) is beneath said threshold value;
iv. returning to step (i) when the determination of the error value of step (iii) is deemed negative.

9. The method according to claim 1 further comprising an identification, said method further comprising:
obtaining an error value between the spectral characteristics of the transformation function and spectral characteristics saved in a database;
wherein an identification is deemed positive if one of the following conditions are met:
I) the error value is beneath a predefined threshold value;
II) the following consecutive steps with possible recursion are fully carried out during a time duration less than a predefined threshold time:
i. transferring the error value to an adaptive filter that adapts the values of one of the spectral characteristics according to the error value;
ii. obtaining an error value between the adapted spectral characteristics value and the other spectral characteristics;
iii. determining if the error value of step (ii) is beneath said threshold value;
iv. returning to step (i) when the determination of the error value of step (iii) is deemed negative.

10. A system comprising one or more cameras connected to processing means, wherein the processing means comprise:
A) a database;
B) a transformation to frequency domain module;
C) a comparing frequency coherence function module;
wherein the processing means are configured to generate a biometric signature of a subject comprising the steps of:
obtaining a plurality of sequential video frame images of a moving subject from a video segment;
obtaining a portion of each frame comprising a surrounding of the moving subject;
wherein obtaining the portion of each frame comprising the surrounding of the moving subject comprises:
obtaining foreground frames corresponding to the plurality of sequential video frames, each comprising the moving subject;
generating a vector representing the direction of the moving subject;
determining a Region Of Interest (ROI) at a position in relation to said vector;
wherein determining the Region Of Interest (ROI) at a position in relation to said vector comprises:
a. obtaining a plurality of background sequential video frames being a sequence of frames comprising the background of the plurality of sequential video frame images;
b. integrating the vector determined in each background frame;
c. determining an initial ROI on each background frame being at a redetermined corresponding position from said vector;
d. carrying out a transformation function to the frequency domain in time to the ROI portions of said background frames obtaining spectral characteristics and determining the stability frequencies from said spectral characteristics;
e. integrating each of the plurality of sequential video frame images with said initial ROI determined and carrying out a transformation function to the frequency domain in time to the initial ROI portion of said sequential video frames thus obtaining spectral characteristics and storing the sensitivity of said stability frequencies of said spectral characteristics of the initial ROI;
f. shifting the initial ROI to a surrounding area in each of the plurality of sequential video frame images, and carrying out a transformation function to the frequency domain in time to the currently shifted ROI portion of said sequential video frames thus obtaining spectral characteristics and storing the sensitivity of said stability frequencies of said spectral characteristics of the currently shifted ROI;
g. repeating the shifting step f for all sequences according to a predetermined shifting rule;
h. after step f has been repeated for all sequences of the shifting rule determining the ROI of the initial and shifted ROIs with the highest sensitivity stored as the ROI; and
determining said portion of each frame comprising the surrounding of the moving subject, at a location on each frame corresponding to the location of said determined ROI;
carrying out a transformation function to the frequency domain on one or more of said portions of the frames comprising the surrounding of the moving subject; and
saving the spectral characteristics of said transformation function in a repository.

11. A method for generating a biometric signature of a subject comprising:
obtaining a plurality of sequential video frame images of a moving subject from a video segment;
obtaining a portion of each frame comprising a surrounding of the moving subject;
wherein obtaining the portion of each frame comprising the surrounding of the moving subject comprises:
obtaining foreground frames corresponding to the plurality of sequential video frames, each comprising the moving subject;
generating a vector representing the direction of the moving subject;
wherein generating the vector representing the direction of the moving subject comprises:
obtaining body portions of the foreground objects of the foreground frames;

wherein the body portions are one or more of:
a head portion;
a center body portion; or
a feet portion;
obtaining reference point frames corresponding to the foreground frames, each comprising a reference point about or at an edge of the corresponding location of said body portions;
combining all the reference points frames into a three-dimensional coordinate system frame comprising all the reference points being at their corresponding location on the three-dimensional coordinate system frame;
determining a vector in the three-dimensional coordinate system frame according to a sequence of a number of reference points from the reference points, that produce the most stable vector;
determining a Region Of Interest (ROI) at a position in relation to said vector; and
determining said portion of each frame comprising the surrounding of the moving subject, at a location on each frame corresponding to the location of said determined ROI;
carrying out a transformation function to the frequency domain on one or more of said portions of the frames comprising the surrounding of the moving subject; and
saving the spectral characteristics of said transformation function in a repository.

12. The method according to claim 11, wherein obtaining foreground frames corresponding to the plurality of sequential video frames comprises:
obtaining a background frame comprising the background of the plurality of sequential video frame images;
subtracting said background frame from each of the plurality of sequential video frames.

13. The method according to claim 11, wherein generating the vector representing the direction of the moving subject comprises:
obtaining body portions of the foreground objects of the foreground frames;
obtaining reference point frames corresponding to the foreground frames, each comprising a reference point about or at an edge of the corresponding location of said body portions;
combining all the reference points frames into a three-dimensional coordinate system frame comprising all the reference points being at their corresponding location on the three-dimensional coordinate system frame;
determining a vector in the three-dimensional coordinate system frame according to a sequence of a number of reference points from the reference points, that produce the most stable vector.

14. The method according to claim 11, wherein determining the Region Of Interest (ROI) at a position in relation to said vector comprises:
a. obtaining a plurality of background sequential video frames being a sequence of frames comprising the background of the plurality of sequential video frame images;
b. integrating the vector determined in each background frame;
c. determining an initial ROI on each background frame being at a predetermined corresponding position from said vector;
d. carrying out a transformation function to the frequency domain in time to the ROI portions of said background frames obtaining spectral characteristics and determining the stability frequencies from said spectral characteristics;
e. integrating each of the plurality of sequential video frame images with said initial ROI determined and carrying out a transformation function to the frequency domain in time to the initial ROI portion of said sequential video frames thus obtaining spectral characteristics and storing the sensitivity of said stability frequencies of said spectral characteristics of the initial ROI;
f. shifting the initial ROI to a surrounding area in each of the plurality of sequential video frame images, and carrying out a transformation function to the frequency domain in time to the currently shifted ROI portion of said sequential video frames thus obtaining spectral characteristics and storing the sensitivity of said stability frequencies of said spectral characteristics of the currently shifted ROI;
g. repeating the shifting step f for all sequences according to a predetermined shifting rule;
h. after step f has been repeated for all sequences of the shifting rule determining the ROI of the initial and shifted ROIs with the highest sensitivity stored as the ROI.

15. The method according to claim 11 further comprising a step of identification by comparing the obtained spectral characteristics of the transformation function with spectral characteristics saved in a database, wherein an identification result is deemed to be positive when the coherence level between both compared frequency spectral characteristics is above a certain threshold.

16. The method according to claim 11 comprising performing a signature for a subject by obtaining and saving the vector generated and the corresponding ROI portion determined, and further obtaining and saving one or more of the following items in a database in relation to said subject:
the spectral characteristics of a transformation function to the frequency domain in time to the ROI portions of the sequential frames;
the spectral characteristics of a transformation function to the frequency domain in time to the ROI portions of the background frames;
the spatial spectral characteristics of a transformation function to the frequency domain at the ROI portion of one of the sequential frames;
the spatial spectral characteristics of a transformation function to the frequency domain at the ROI portion of one of the background frames.

17. The method according to claim 11, further comprising a step of identification;
providing a signature of a subject person stored in a data base comprising a vector, an ROI, spectral characteristics of a transformation function to the frequency domain in time of a frame sequence, spectral characteristics of a transformation function to the frequency domain in time of background frames;
wherein the Region Of Interest (ROI) at a position in relation to the vector is determined such that it is in the same position in relation to the vector as the signature ROI in relation to the signature vector;
wherein said method further comprises:
i. obtaining the spectral characteristics of a transformation function to the frequency domain in time to the ROI portions of the background frames;

ii. obtaining a relative difference by inputting the spectral characteristics of a transformation function to the frequency domain in time of the background frames of step (i) and said signature spectral characteristics of a transformation function to the frequency domain in time of background frames, into a transfer function;

iii. obtaining the spectral characteristics of a transformation function to the frequency domain in time to the ROI portions of the sequence frames and shifting the value of said spectral characteristics of a transformation function to the frequency domain in time to the ROI portions of the sequence frames, in a proportional manner as said relative difference;

iv. comparing the shifted values to the signature spectral characteristics of a transformation function to the frequency domain in time of a frame sequence;

wherein an identification result is deemed to be positive when the coherence level between the compared spectral characteristics of step (iv) is above a predefined threshold.

18. The method according to claim 11 further comprising an identification, said method further comprising:

obtaining an error value between the spectral characteristics of the transformation function and spectral characteristics saved in a database;

wherein an identification is deemed positive if one of the following conditions are met:

I) the error value is beneath a predefined threshold value;

II) the following consecutive steps are carried out less times than a predetermined threshold number:
  i. transferring the error value to an adaptive filter that adapts the values of one of the spectral characteristics according to the error value;
  ii. obtaining an error value between the adapted spectral characteristics value and the other spectral characteristics;
  iii. determining if the error value of step (ii) is beneath said threshold value;
  iv. returning to step (i) when the determination of the error value of step (iii) is deemed negative.

19. The method according to claim 11 further comprising an identification, said method further comprising:

obtaining an error value between the spectral characteristics of the transformation function and spectral characteristics saved in a database;

wherein an identification is deemed positive if one of the following conditions are met:

I) the error value is beneath a predefined threshold value;

II) the following consecutive steps with possible recursion are fully carried out during a time duration less than a predefined threshold time:
  i. transferring the error value to an adaptive filter that adapts the values of one of the spectral characteristics according to the error value;
  ii. obtaining an error value between the adapted spectral characteristics value and the other spectral characteristics;
  iii. determining if the error value of step (ii) is beneath said threshold value;
  iv. returning to step (i) when the determination of the error value of step (iii) is deemed negative.

* * * * *